United States Patent [19]
Benefiel et al.

[11] Patent Number: 4,981,468
[45] Date of Patent: Jan. 1, 1991

[54] DELIVERY DEVICE FOR ORALLY ADMINISTERED THERAPEUTIC AGENTS

[75] Inventors: Robert L. Benefiel, Greenfield; John W. Clarke, Indianapolis; Dale C. Harris, Fairland; Robert J. Morff, Indianapolis; Peter L. Oren, Fishers, all of Ind.

[73] Assignee: Eli Lilly and Company, Indianapolis, Ind.

[21] Appl. No.: 464,481

[22] Filed: Jan. 12, 1990

Related U.S. Application Data

[63] Continuation-in-part of Ser. No. 312,636, Feb. 17, 1989.

[51] Int. Cl.[5] .............................................. A61M 37/00
[52] U.S. Cl. .......................................... 604/83; 604/84
[58] Field of Search ....................... 604/77, 78, 82, 83, 604/84, 85; 239/33

[56] References Cited

U.S. PATENT DOCUMENTS

| | | | |
|---|---|---|---|
| 121,684 | 12/1871 | Sullivan . | |
| 430,928 | 6/1890 | Doty . | |
| 580,527 | 4/1897 | Martin . | |
| 697,209 | 4/1902 | Koppenhagen . | |
| 1,236,029 | 8/1917 | Williams . | |
| 1,685,280 | 9/1928 | Findley . | |
| 2,436,505 | 2/1948 | Du Rall . | |
| 2,753,267 | 7/1956 | Rabin et al. | 99/138 |
| 2,846,313 | 8/1958 | Menkin et al. | 99/138 |
| 3,517,884 | 6/1970 | Horvath | 239/33 |
| 3,615,595 | 10/1971 | Guttag | 99/138 R |
| 3,905,477 | 9/1975 | Graham | 206/459 |
| 3,980,074 | 9/1976 | Watt et al. . | |
| 4,440,207 | 4/1984 | Genatempo et al. | 150/52 |
| 4,581,013 | 4/1986 | Allen | 604/78 |
| 4,792,333 | 12/1988 | Kidder | 604/83 |

*Primary Examiner*—John D. Yasko
*Attorney, Agent, or Firm*—Nancy J. Harrison; Steven R. Lammert; Leroy Whitaker

[57] ABSTRACT

An improved device for containing and administering orally active therapeutic agents is described. A unit dose of a therapeutic agent in free-flowing form is retained and positioned for oral administration in a tube adapted to deliver the dose with a flow of liquid drawn through the tube by normal sipping action of a patient. The combination of small particle size and high flow rates into the alimentary canal allow dosage administration with minimal sensed contact with the oral cavity. The invention is particularly advantageous for the administration of orally active therapeutic agents to pediatric and geriatric patients.

21 Claims, 3 Drawing Sheets

DELIVERY DEVICE FOR ORALLY ADMINISTERED THERAPEUTIC AGENTS

CROSS REFERENCE TO RELATED APPLICATIONS

This application is a continuation-in-part of allowed U.S. application Ser. No. 07/312,636, filed Feb. 17, 1989 pending.

FIELD OF THE INVENTION

This invention relates to an improved delivery device and method for oral administration of therapeutic agents. More particularly, this invention is directed to a device which enables oral administration of pharmaceuticals with minimal sensed contact with the oral cavity. The present device further provides a convenient packaged unit dosage form for use at home or hospital. It yields particular advantage for administration of oral therapeutics to both pediatric and geriatric patients.

BACKGROUND OF THE INVENTION

Many commercially significant therapeutic agents are effective by the oral route of administration. Generally speaking, orally administered tablets and capsules are the most convenient, and most patient favored dosage forms. Nonetheless, there are many patients either unable or simply unwilling to take such orally administered medications. For some patients, the perception of unacceptable taste or mouth feel of a dose of medicine leads to a reflex action that makes swallowing difficult or impossible. Thus, there are many patients, including particularly pediatric and geriatric patients, that find it difficult to ingest the typical solid oral dosage forms of therapeutic agents such as compressed tablets or capsules.

Accordingly, there has been a significant research and development effort directed to the identification of alternate acceptable oral dosage formulations. Thus, for example, flavored solutions/suspensions of some therapeutic agents have been developed to facilitate the oral administration of such agents to patients normally having difficulty ingesting conventional solid oral dosage forms. While liquid formulations are more easily administered to the problem patient, liquid/suspension formulations are not without their own significant problems and restrictions. Firstly, the dose amount is not so easily controlled as with tablet and capsule forms. Secondly, many therapeutic agents are simply not sufficiently stable in solution/suspension form. Indeed, most suspension type formulations are typically reconstituted by the pharmacist and then have a limited shelf life even under refrigerated conditions. Another problem with liquid formulations which is not so much a factor for conventional solid oral dosage forms such as tablets and capsules is the taste of the active agent. The taste of some therapeutic agents is so unacceptable that liquid formulations are simply out of the question. Finally, solution/suspension type formulations are typically not acceptable where the active agent must be provided with a protective coating, e.g. a taste masking coating or an enteric coating to protect the active agent from the strongly acidic conditions of the stomach.

Particulate or pelletized forms of therapeutic agents, optionally having functional coatings, have been available either for filling capsules or in packets from which a patient can sprinkle the particulate/pelletized dose onto soft food. While use of such particulate dosage forms as a "sprinkle" composition for use on food does facilitate oral administration, that dosage methodology is also not without its limitations. The food itself can interact with the functional coatings typically used on such dosage forms to dissolve or otherwise disrupt the coating prematurely. Depending on the purpose of the coating, its premature disruption can adversely affect therapeutic efficacy and/or the taste of the food. Coating disruption can likewise occur in the mouth. The grittiness a patient encounters when utilizing "sprinkle" dosage forms on soft food encourages chewing.

In addition to the above referenced efforts to develop alternate dosage forms as a means for facilitating oral administration of therapeutic agents, the patent literature evidences efforts to develop devices intended to facilitate the oral administration of conventional solid oral dosage forms (tablets and capsules).

DuRall U.S. Pat. No. 2,436,505 describes a generally tubular straw-like device having an expanded mouthpiece for retaining the solid medication for oral administration. The device is utilized by inhaling a liquid through the tubular member similar to the normal use of a straw.

Koppenhagen U.S. Pat. No. 697,209 discloses a device for containing a liquid and suspending a solid medication. The liquid and solid medication are ingested by turning the device upright to allow the liquid and medication to move into the mouth by the force of gravity.

Sullivan U.S. Pat. No. 121,684 describes a device generally in the form of a kettle having a means for insertion of a solid medication into its spout. The spout is taken into the mouth for ingesting the liquid therein while a solid medication is inserted into the spout for flow into the oral cavity along with the stream of liquid.

Allen U.S. Pat. No. 4,581,013 describes and claims a dosing device for facilitating the oral administration of solid medicines, particularly tablets and capsules.

Notwithstanding the progress that has been made in the development of new oral dosage forms and devices to facilitate administration of old dosage forms, there is still much room for improvement in this technology area.

Accordingly, it is an object of this invention to provide an improved device for the oral administration of a dose of a therapeutic agent.

It is a further object of this invention to provide a method for administering a predetermined dose of a therapeutic agent in particulate dosage form with minimal sensed contact of the therapeutic agent with the oral cavity and with minimal disruption of functional coatings, if any, on said particulate dosage form.

It is still another object of this invention to provide an oral active therapeutic agent in a unit dosage form, packaged in a tube configured to facilitate the oral administrative of the contained therapeutic agent.

These and other objects are accomplished in accordance with this invention by use of a delivery device in the form of a tube adapted or configured to retain a unit dose of a therapeutic agent in a free-flowing form for contact with and vertical displacement by a fluid drawn through the tube by the normal sipping action of a patient. The delivery tube has a fluid inlet end and a fluid outlet end and can be constructed to have a particle retaining means in contact with the inner walls of the tube and located at a point between the fluid inlet and fluid outlet ends of the tube. The retaining means is typically constructed as a fluid permeable grid in the form of a weave, mesh, screen, sieve or slat construction. The grid is constructed to have a surface area greater than the minimum luminal cross-sectional area of the tube at any point along its length. The grid is typically constructed so that at least a portion of the grid forms an acute angle with a line parallel to the longitudinal axis of the tube. In one preferred embodiment the grid is a planar structure and has a surface area greater than the cross-sectional area of the tube at its outlet end. The therapeutic agent is located in particulate form between the grid and the outlet end of the tube. Either one or both of the ends of the tube can be adapted to receive one end of a drinking straw.

Alternatively, the tube can be configured to retain a dose of therapeutic agent in an axially discrete portion of the tube having a local gravitational potential minimum relative to adjacent axial portions of the tube when the tube is in position for oral administration of the contained dose.

In each embodiment of this invention the device is designed to allow a maximum rate of liquid flow through the tube when the liquid outlet end is placed in a patient's mouth and the patient draws liquid into the inlet end of the tube with a normal sipping action. Optionally, each embodiment of this invention is provided removable means for sealing the therapeutic agent in the tube, thus providing a convenient package form for the contained unit dose.

Use of the pharmaceutical delivery device in accordance with this invention requires that the patient place the outlet end of the tube in his mouth and the inlet end in a liquid reservoir. Normal sipping action of the patient results in the rapid and smooth flow of the therapeutic agent and the carrier liquid into the alimentary canal of the patient with minimal sensed contact of the therapeutic agent with the oral cavity.

DETAILED DESCRIPTION OF THE INVENTION

Figure 1:
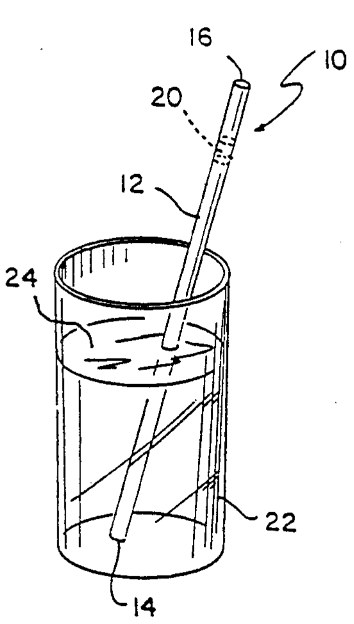
FIG. 1 is a perspective view of a device in accordance with this invention in a liquid reservoir.

This invention is directed to a device designed to facilitate the oral administration of multiparticulate dosage forms of therapeutic agents. Use of the device enables the oral administration of a particulate dosage form with minimal pre-administration contact time with coating disrupting agents (such as food) and with minimal sensed contact of the dosage form with the oral cavity. Such minimizes the possibility of disruption of the functional coatings often used on multiparticulate dosage forms. The device is constructed to deliver a therapeutic dose into a patient's alimentary canal in a free-flowing form (derived from reduced particle size), carried in a rapidly flowing narrow stream of liquid directed at the back of the oral cavity, by the normal sipping action of a patient.

A unit dose of a therapeutic agent is retained and positioned for oral administration in a tubular structure having a liquid inlet end and a liquid outlet end. The means for retaining the therapeutic agent in the tube is selected and designed to minimize resistance to the flow of fluid through the tube structure. It is important for satisfactory delivery of a therapeutic agent in the form contemplated herein that the flow rate be sufficient under conditions of suction associated with normal sipping (as through a drinking straw) to carry the therapeutic agent in a bolus-like fashion up through the tube outlet and quickly through the patient's mouth and into his throat with minimal sensory detection of the administered dose.

The device of the present invention is designed to facilitate the oral administration of a dose of a therapeutic agent in a flow of liquid drawn by a patient through a tube having a liquid inlet end and a liquid outlet end and means for supporting the dose between the tube ends. The improvement in accordance with this invention provides an effective means for supporting a dose of a therapeutic agent in a free-flowing form in a tube for oral administration while providing minimal resistance to fluid flow through the tube under the influence of a patient's normal sipping action. This is accomplished either (1) by positioning a grid in the tube so that at least a portion of the grid forms an acute angle with a line parallel to the longitudinal axis of the tube, thereby increasing the effective grid cross sectional area, (2) by locating the grid in a portion of the tube having increased luminal cross-sectional area, or (3) by forming the tube to have a longitudinal conformation such that the tube, when positioned for oral administration of the contained therapeutic agent, has at least one axially discrete portion between its inlet and outlet ends having a local gravitational potential minimum relative to adjacent axial portions of the tube. In that latter construction, the dose of therapeutic agent is gravimetrically retained or supported in the portion of the tube with the gravitational potential minimum thereby eliminating the need for a grid construction, and providing essentially no resistance to fluid flow under the influence of a patient's sipping action.

In accordance with one embodiment of this invention the therapeutic agent is supported in the tube by a grid having a mesh size small enough to support the therapeutic agent in particulate form. One problem associated with such construction derives from the resistance that a small mesh grid imposes on fluid flow through the tube. Thus, while it is desirable to minimize particle size of the therapeutic agent to reduce probability of sensed contact of same with the oral cavity, the grid size necessary to support such a particulate dosage form often does not allow satisfactory fluid flow rates through the tube to carry the therapeutic agent through the tube outlet and through the oral cavity of the patient with the desired minimal sensed perception of the therapeutic agent being administered. A small mesh grid positioned across the internal diameter of the tube reduces the rate of fluid flow responsive to normal sipping action by the patient and thus reduces the capacity of the fluid to carry the particulate dose form cleanly through the tube outlet and into the oral cavity of the patient; the velocity of the fluid flow is such that it is inadequate to carry or wash the retained particulate dose in the desired bolus-like fashion through the oral cavity and into the throat. With reduced flow rates in the tube the particles tend to become mixed and suspended in the volume of liquid in the tube between the supporting grid and the tube outlet, requiring the patient to sip a significantly larger volume of fluid to carry the dose into the throat. While the problems associated with reduced flow rates can be reduced by increasing the grid mesh size and/or by minimizing the distance between the dose supporting grid and the outlet end of the tube, the use of necessarily larger particles and the reduced rate of flow still increase the probability of sensory perception of that dose by the patient.

The grid is constructed to have a surface area greater than the minimum luminal cross-sectional area of the tube along its length. It can present a planar or a non-planar surface. Preferably, planar grids are positioned to contact the tube at points on its internal diameter at varying distances from the outlet end of the tube. Alternatively they can be positioned in a portion of a tube having some point of increased luminal cross-sectional area. Regardless of the surface configuration of the grid, it is preferred that the grid be positioned in the tube more proximal to its outlet end than its inlet end.

The conformed-tube embodiment of the device in accordance with this invention can be formed to have a wide variety of longitudinal conformations. In its simplest form it is contemplated that the device is constructed in the form of a tube wherein at least a portion of the tube forms at least one complete loop. Alternatively, the longitudinal confirmation of the tube can be such that there is a generally U-shaped portion of the tube which forms a localized gravitational potential minimum for containing the therapeutic agent when the tube is positioned for oral administration of the contained therapeutic agent. The conformed-tube embodiment of this invention can be utilized to contain and administer liquid/suspension formulations of therapeutic agents as well as therapeutic agents in particulate or pelletized form.

The form of the dose of therapeutic agent to be administered in accordance with this invention, i.e., in a free-flowing form, itself contributes to the functionality of the present device and method. A "free-flowing form" as used herein is one that will generally allow the dose itself, in the aggregate, to assume the shape of its container. This property is important functionally in this invention in that the property not only allows the aggregate dose to be easily positioned to a retained position in the present device embodiment for delivery to a patient, but it also allows the aggregate dose to assume the conformation of its immediate environment as it passes through the mouth and into the throat of the patient In a free-flowing solid form as opposed to a conventional solid oral dosage form, the dose is less likely to exert detectable (sensed) contact with the oral cavity.

It is contemplated that each of the tubular delivery device embodiments of this invention can serve not only as a means for delivering orally active therapeutic agents but also as a shipping container or package for each unit dose of therapeutic agent. Thus, the therapeutic agent can be manufactured in a form suitable for administration utilizing the device in accordance with this invention and filled into the delivery device in an amount corresponding to a unit dose of the therapeutic agent. The inlet and outlet ends of the tube can be heat sealed or sealed with a plug or a cap construction which can be removed by the patient or medical attendant immediately before usage of the device to administer the contained dose.

Further, the inlet and/or outlets ends of the tube can be adapted to receive, in fluid tight engagement, one end of a drinking straw to facilitate use of the device. Thus, it is contemplated as one embodiment of the present invention that the device/packaged dosage form in accordance with this invention can be in the form essentially of a tubular mouth piece for the end of a drinking straw wherein the inlet end of the mouth piece is adapted to receive one end of a drinking straw.

It is contemplated as well that the present device can include a one-way valve such as flap valve, a duck-bill valve or a ball-and-seat-type arrangement to prevent possible siphoning of the therapeutic agent out the inlet end of the tube into the liquid should the patient's sipping action be stopped before dose administration is complete. Experience to date, however, indicates that such a valve is not a critical component of the present device.

To utilize the present device, a patient is instructed to position the outlet end of the tube in the patient's mouth and to draw liquid through the tube to carry the therapeutic agent into the patient's alimentary canal with minimal sensed contact with the patient's oral cavity.

Figure 2:
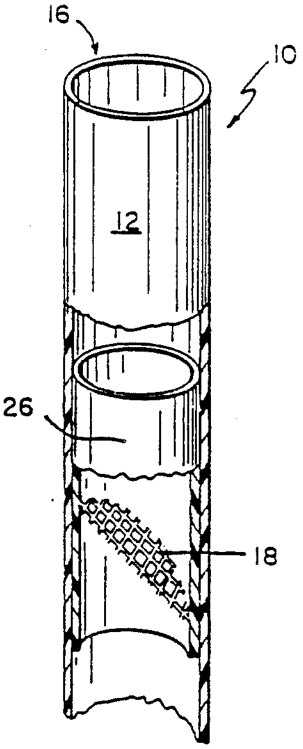
FIG. 2 is a partial cross-sectional view of the device illustrated in FIG. 1.
Figure 3:
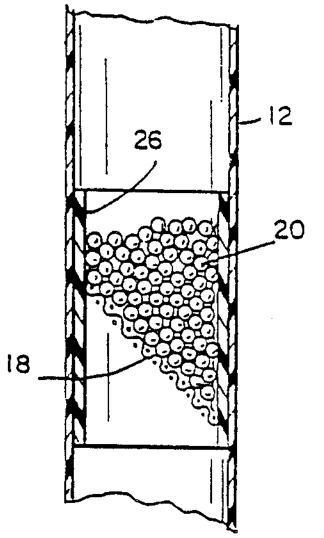
FIG. 3 is a partial tranverse-sectional view of a device similar to that in FIG. 2 with a particulate therapeutic agent in position for delivery.

One device embodiment of the present invention is illustrated in FIGS. 1–3. FIG. 1 shows the device in position for use. Delivery device 10 includes a tube 12 having liquid inlet end 14 and liquid outlet end 16 and a grid 18 for supporting the unit dose of the therapeutic agent 20 (FIG. 3) in tube 12. Delivery device 10 is positioned with its inlet end 14 in reservoir 22 containing consumable liquid 24. The patient can ingest therapeutic agent 20 in accordance with this invention by placing his mouth over the outlet end 16 of tube 12 and sipping a small volume of consumable liquid 24. Therapeutic agent 20 is carried by liquid 24 moving up tube 12 into the patient's alimentary canal with minimal sensed contact of the therapeutic agent with the patient's oral cavity.

Tube 12 can be manufactured from a wide variety of commercially available plastics as are commonly used in the manufacturer of drinking straws and include materials such as delrin, polypropylene, polyethylene, polyesters, or fluorocarbons. The optical properties of the material used to form tube 12 can be a factor in some embodiments of this invention. Thus, for some patient applications and in some device configurations it may be important for the tube to be transparent or translucent to enable visual inspection of therapeutic agent 20 supported in tube 12. In other patient applications it may be desirable to use opaque materials so that the therapeutic agent cannot be visualized by the patient. The mechanical properties and dimensions of tube 12 can be widely varied while still retaining delivery device functionality in accordance with this invention.

With reference to FIG. 2 and 3, grid 18 is provided for retaining therapeutic agent 20. Grid 18 is mounted in sleeve 26 immobilized in tube 12. Grid 18 is positioned so that when sleeve 26 is located in tube 12 at least a portion of grid 18 forms an acute angle with a line parallel to the longitudinal axis of tube 12. Grid 18 has a mesh size sufficiently small to support the smallest granules or particles of therapeutic agent 20. Grid 18 is positioned in tube 12 near its outlet end 16. The volume of tube 12 between grid 18 and outlet end 16 is sufficient to contain an amount of therapeutic agent 20 corresponding to a unit dose thereof.

Grid 18 and sleeve 26 can be constructed from the same or different materials used for construction of tube 12. A suitable grid mesh can be formed from wire, e.g., stainless steel screen or of cast or injection molded plastics, including cellulosic materials, nylon, polyester, polyethylene, polypropylene and fluorocarbons (Teflon). The grid should be constructed so as to have maximal open area for liquid passage yet able to retain the selected pellets or granules. The mesh size can range from about 140 mesh to about 10 mesh, more preferably from about 80 mesh to about 10 mesh.

Figure 4:
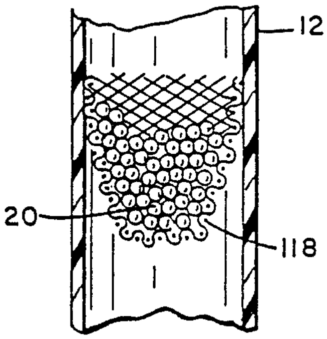
FIG. 4 is a partial cross-sectional view of another device of this invention incorporating a modification of the grid structure.

FIG. 4 illustrates use of a basket shaped grid 118, located in tube 12 for retaining particulate or pelletized therapeutic agent 20.

Figure 5:
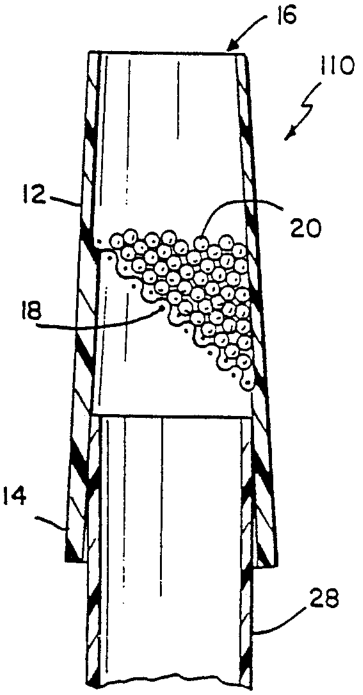
FIG. 5 is a cross-sectional view of a mouthpiece of this invention positioned on the end of a drinking straw.

As illustrated in FIG. 5 the pharmaceutical delivery device of this invention can be constructed in the form of a mouthpiece for use in conjunction with a commercially available drinking straw 28. Delivery device 110 is in the form of a mouthpiece and has an angled grid 18 for supporting particulate or pelletized therapeutic agent 20 in tube 12 having inlet end 14 and outlet end 16. Inlet end 14 is adapted to receive one end of drinking straw 28 in a fluid tight relationship.

It is not critical that tube 12 of delivery devices 10, 110 be of a strictly linear construction. Thus, tube 12 may be angled, curved or flexible to facilitate positioning of outlet end 16 in the mouth of a patient while inlet end 14 is positioned in a reservoir containing a consumable liquid or joined with a drinking straw placed in such a reservoir. Nor is it critical that tube 12 of delivery device 10, 110 be of constant luminal cross-sectional area throughout its entire length.

Figure 6:
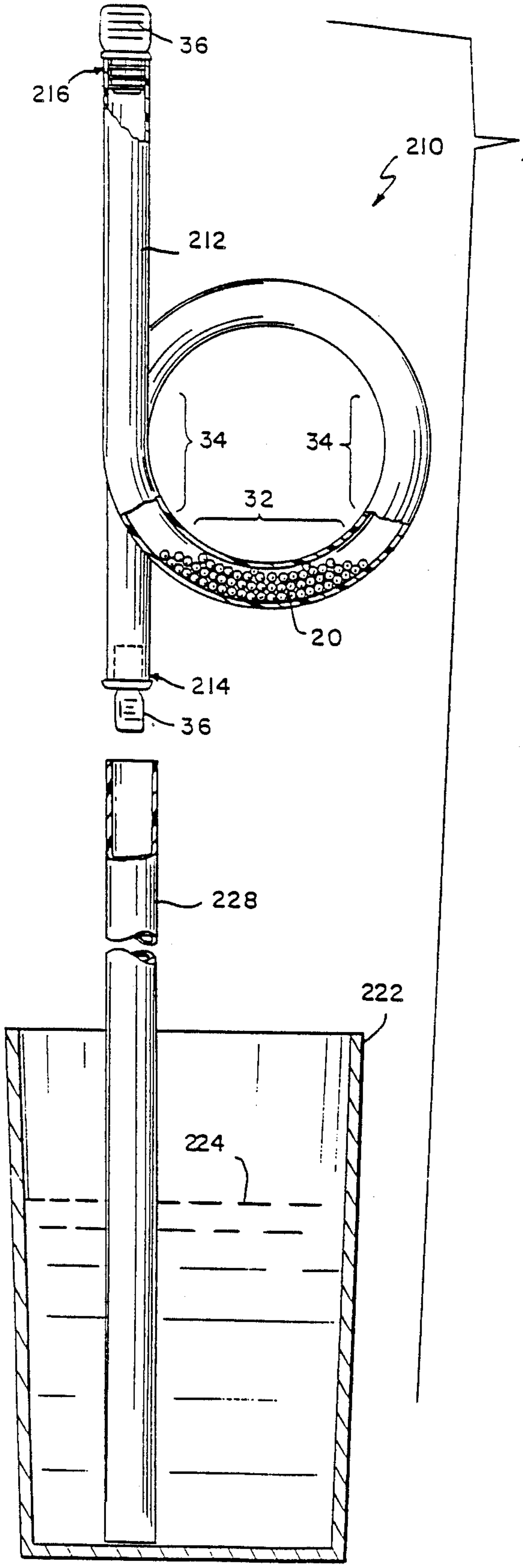
FIG. 6 is an elevational view of another embodiment of this invention with portions broken away.
Figure 7:
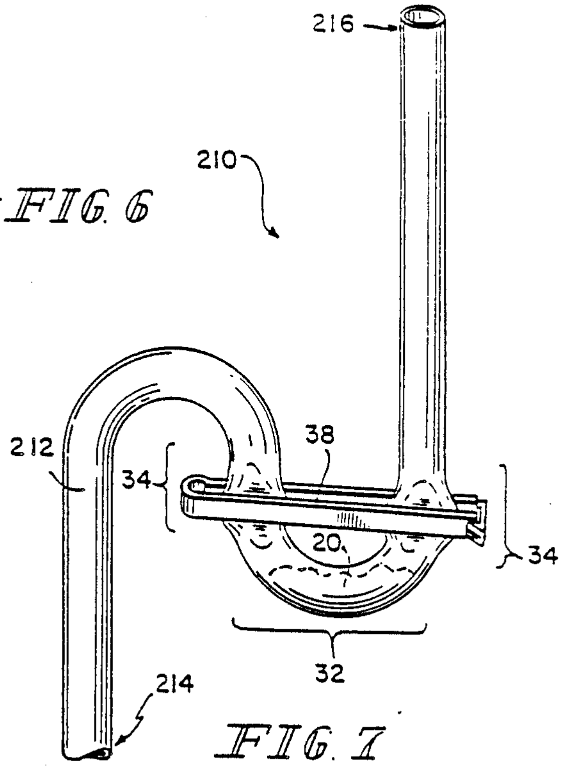
FIG. 7 is a sideview of another embodiment of this invention with a clamp closure.

Alternate embodiments of this invention are illustrated in FIGS. 6 and 7. Prepackaged unit dose 210 contains a therapeutic agent for oral administration. A unit dose of therapeutic agent 20 is contained in curved tube 212 having liquid inlet end 214 and liquid outlet end 216. Tube 212 has a longitudinal conformation such that when tube 212 is positioned (as shown) for oral administration of therapeutic agent 20 there exists an axially discrete portion 32 between inlet end 214 and outlet end 216 having a local gravitational potential minimum relative to adjacent axial portions 34 of tube 212. Axially discrete portion 32 of tube 212 is of sufficient volume to contain and retain the unit dose of therapeutic agent 20 when tube 212 is positioned for oral administration of therapeutic agent 20.

With reference particularly to FIG. 6, inlet end 214 of tube 212 is sized to frictionally engage in a fluid tight relationship with one end of drinking straw 228 positioned in reservoir 222 containing consumable liquid 224. The unit dose 210 illustrated in FIGS. 6 and 7 are each provided with removable means for retaining therapeutic agent 20 in tube 212 when the tube is not positioned for oral administration of the contained therapeutic agent. The unit dose 210 of FIG. 6 is provided with removable caps 36 for both outlet end 216 and inlet end 214 of tube 212. In the unit dose 210 shown in FIG. 7 therapeutic agent 20 is sealed in tube 212 by a removable tube-pinching clip 38.

Figure 8:
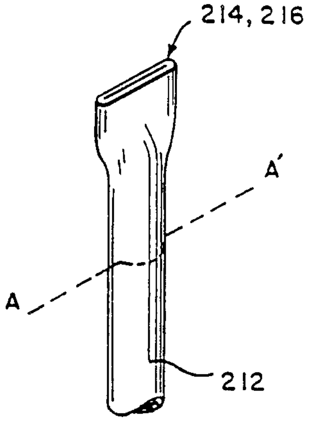
FIG. 8 illustrates a sealed end of a device of this invention.

FIG. 8 illustrates a tube end adhesively sealed or heat sealed. Tube ends sealed as illustrated in FIG. 8 can be opened either by cutting the tube, for example with scissors at line A-A', or the tube can be scored proximal to the heat sealed end to provide a weakened fracture line at which the sealed tube end can be separated from the remainder of the tube. The tube sealing or closure means depicted in each of FIGS. 6–8 may be applied in similar fashion to seal the inlet and outlet ends of the delivery devices illustrated in FIGS. 1–5.

Figure 9:
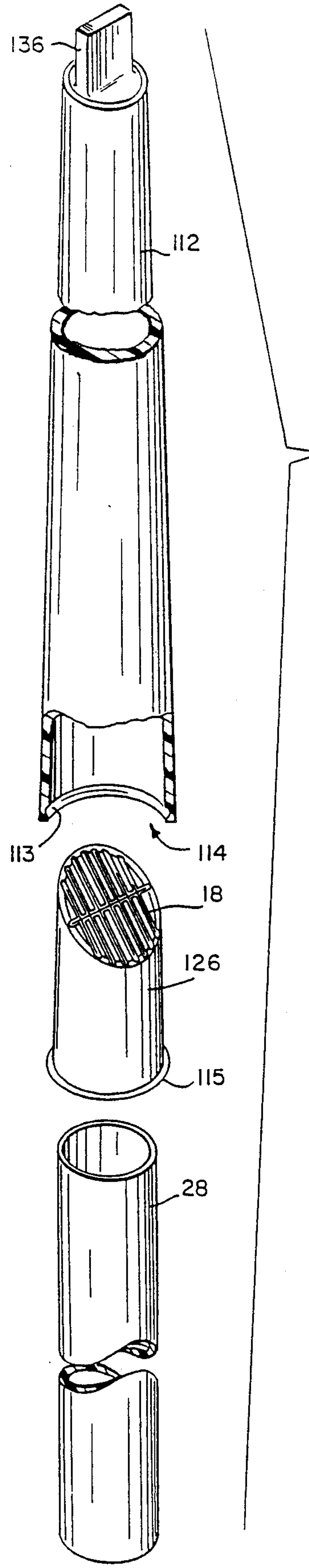
FIG. 9 is an enlarged exploded view of a device of this invention with portions broken away.

With reference to FIG. 9, tube 112 is formed with integral breakaway closure cap 136 at its outlet end 116. Inlet end 114 of tube 112 is formed to receive sleeve 126 supporting grid 18 with a surface area greater than the luminal cross-sectional area of tube 112. The outer diameter of sleeve 126 is sized for friction fit in the inner diameter of tube 112 at inlet end 114. Sleeve 126 is also formed to have circumferential bead 115 positioned for interference fit with annular channel 113 when sleeve 126 is inserted into inlet end 114 of tube 112. The internal diameter of sleeve 126 is formed to receive one end of straw 28 in a fluid-tight, friction-fit arrangement.

Figure 10:
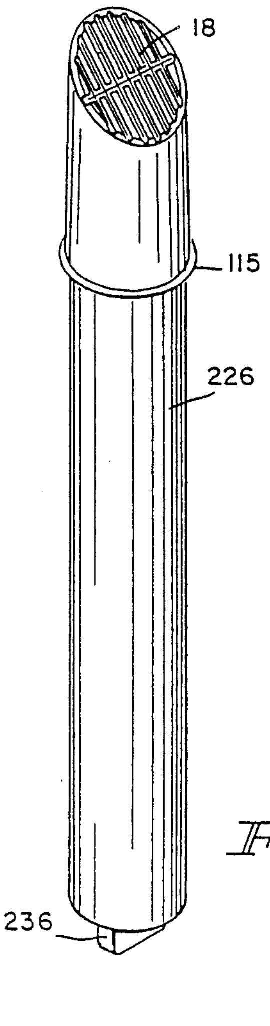
FIG. 10 illustrates an elongated grid-supporting sleeve for use in the delivery device.
Figure 11:
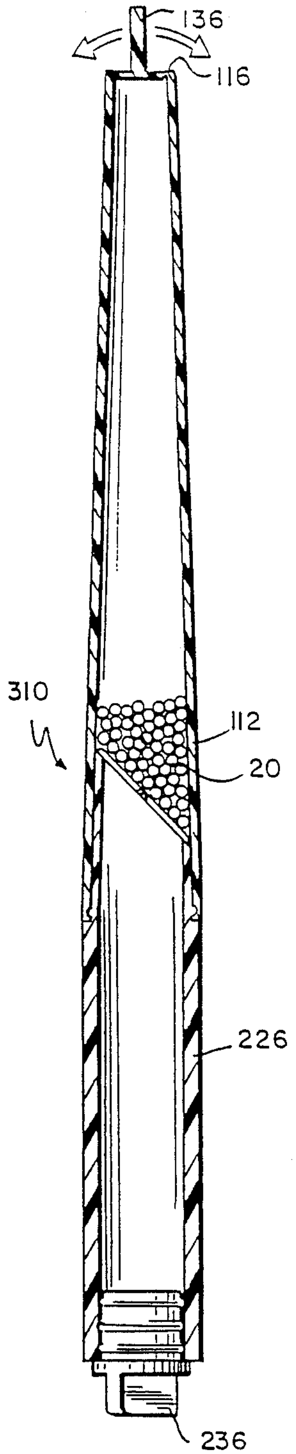
FIG. 11 is a sectional view of a device assembled with the sleeve shown in FIG. 10 with therapeutic agent.

FIG. 10 illustrates an elongated sleeve 226 having grid 18 and removable closure 236. Sleeve 226 is formed to have a circumferential bead 115 proximal to the grid-bearing end of the sleeve for engagement with annular channel 113 on the internal diameter of tube 112 (FIG. 9) upon insertion of sleeve 226 into inlet end 114 of tube 112. A sealed oral dosage form 310 (FIG. 11) of a therapeutic agent 20 in free flowing particulate form can thus be prepared by inverting tube 112 (FIG. 9) having breakaway closure cap 136, filling inverted tube 112 with an amount of said therapeutic agent corresponding to a unit oral dose, and finally inserting the grid-bearing end of sleeve 226 (FIG. 10) into inlet end 114 of tube 112 (FIG. 9) so that bead 115 on sleeve 226 (FIG. 10) engages with an interference fit with annular channel 113 at inlet end 114 of tube 112. To use sealed oral dosage form 310 a patient removes closure cap 236 and thereafter, with outlet end 116 up, he removes upper closure 136. The contained dose of therapeutic agent 20 is carried through the patient's mouth with minimal sensed contact with the oral cavity as the patient places outlet end 116 of the device in his mouth and sips a liquid through elongated sleeve 226 and tube 112.

The unit dosage forms/delivery devices in accordance with this invention are used both as sealed containers for storage and shipping of unit doses of therapeutic agents and also as devices for facilitating oral administration of the contained therapeutic agents. Thus, a device of this invention can be manufactured and shipped as a sealed tube containing an amount of a therapeutic agent corresponding to a unit dose of said agent.

To use the device for drug delivery the patient first positions the tube so that the entire dose of therapeutic agent is either (1) supported in the local gravitational minimum of the tube or (2) supported on the grid when the tube is in a position for oral administration of the contained therapeutic agent. The outlet and inlet ends of the tube are then opened and the inlet end is either submerged in a consumable liquid or fitted on one end of a drinking straw positioned in a container of consumable liquid. The dose of therapeutic agent is administered with minimal sensed contact with oral cavity by the patient placing the outlet end of the tube in his mouth and sipping the consumable liquid through the tube.

The therapeutic agent used in the present invention is preferably in a free-flowing particulate, granular or pelletized form. Therapeutic agents formed as particles, granules or pellets having an average diameter of between about 100 and about 2000 microns are especially suited for administration in accordance with the present invention. The particles, granules or pellets can be optionally coated, for example, to mask taste, to protect the therapeutic agent from stomach acidity or to prolong release of the agent in the intestinal tract.

It is noted that the conformed tube embodiment of this invention, while illustrated with a particulate therapeutic agent, has application as well for the administration of therapeutic agents in the form of solutions or suspensions. For that embodiment it is important only that the therapeutic agent be in a form that can be easily moved axially along the length of the tube and into the locus of gravitational potential minimum as the tube is readied for dosage administration.

The preferred particulate or pelletized form of therapeutic agent for administration in accordance with this invention can be prepared by methods known in the art such as that disclosed in U.S. Pat. No. 4,587,118, which describes the preparation of sustained release theophylline pellets. Drug-coated pellets are prepared by coating sucrose-starch non-pareils with an active therapeutic agent. If a small concentration of the drug is to be applied, the drug may be dissolved or suspended in an appropriate vehicle which may contain a pharmaceutically acceptable binder. The resulting solution/suspension is then sprayed onto sucrose-starch non-pareils of an appropriate mesh size in a conventional coating pan, an accela-cota coating pan, a fluid-bed coating system, such as an Aromatic system or a Glatt system, or other equipment suitable for the coating of small particles.

If higher drug concentrations are desirable, the active agent can be finely divided and layered onto the sucrose-starch non-pareils using conventional pharmaceutical binders. In this method sugar coating binder systems, such as sucrose and acacia, have been used successfully in the past. The active agent is applied to the non-pareils by applying the binder solution, allowing the pellets to become evenly coated and then applying the active agent as a dry powder. This process is continued until the desired quantity of active agent has been applied. In this manner, pellets having up to 70% by weight of the drug can be formed.

The drug-coated pellets resulting from that method of manufacture will typically possess a very uniform particle size distribution and smooth pellet surface. These pellets are excellent candidates for coating to provide sustained release, gastric protection or taste masking.

Numerous coatings for the purpose of providing sustained release of.an active agent are also known. These include, but are not limited to, acrylic resins, ethylcellulose, ethylcellulose in combination with hydroxypropyl methylcellulose, or a latex emulsion.

Many polymers are also available for the purpose of protecting a drug from gastric destruction and/or preventing the active agent from irritating the gastric mucosa. These include the acrylic resins, cellulose acetate phthalate, polyvinyl acetate phthalate, or hydroxypropyl methylcellulose phthalate.

Taste masking of a pelletized formulation can be accomplished by coating with one of a number of polymers well known to the pharmaceutical chemist, including Eudragit E, hydroxypropyl methylcellulose, hydroxypropyl cellulose, gelatin, or polyethylene glycols.

The above polymers can be used alone or in combination and may be modified by the addition of other coating adjuncts including plasticizers, anti-tacking agents, or colorants. These coating systems may be applied to the active core pellets as described above for the preparation of the core pellets.

Marume formation is another method of preparing a therapeutic agent for use in the present invention. The active drug and any excipients or binders would be blended in an appropriate mixer and granulated. The resulting wet mass is extruded through a perforated screen or plate to yield strands of material which ideally should break apart easily. These short strands are then spheronized using a marumerizer or equivalent piece of equipment which rotates at high speeds and results in small spheres or rounded rods of uniform particle size. These marumes are then dried and sieved to remove undersized and oversized particles or agglomerates. Particles prepared by this process have a narrow particle size distribution, which is determined by the choice of screen used during extrusion. In addition, the marumes typically have a smooth surface which allows the particles to be easily coated to provide extended release, gastric resistance or taste masking. An example of the use of this technology to prepare both immediate release and sustained release marumes is presented in U.S. Pat. No. 4,137,626 (Dempski et al.), which describes the preparation of a sustained release indomethacin formulation.

Wet and dry granulation techniques can also be used to prepare particulate/granular forms of therapeutic agents suitable for administration in accordance with this invention. Drug particles prepared by wet or dry granulation techniques often possess an irregular surface and a relatively wide particle size distribution. Both of these characteristics make the successful coating of granules very difficult. For this reason, a granular form of therapeutic agent would be most appropriate only for those drugs that do not require a coating for taste masking, sustained release or gastric protection. Wet and dry granulation techniques are well-known in the art.

The active agent may be any compound which is suitable for oral administration. For children, it would be especially appropriate for antibiotics such as loracarbef, cefaclor, cephalexin, amoxicillin, ampicillin, penicillin V, cefadroxil, cefuroxime axetil, erythromycin, dirithromycin, sulfamethoxazole/ trimethoprim, analgesic agents such as aspirin, ibuprofen and acetaminophen, or bronchodilators such as theophylline and albuterol.

For geriatric and other patients, examples of the types of therapeutic agents which might benefit from this type of delivery system are exemplified by, but not limited to, the following classes of therapeutic agents:

Beta-blockers such as propranolol, metoprolol, atenolol, labetolol, timolol, penbutolol, and pindolol; antimicrobial agents such as those described above and ciprofloxacin, cinoxacin, and norfloxacin; antihypertensive agents such as clonidine, methyldopa, prazosin, verapamil, nifedipine, captopril, and enalapril; antihistamines such as chlorpheniramine and brompheniramine; tranquilizers such as diazepam, chordiazepoxide, oxazepam, alprazolam, and triazolam; anti-depressants such as fluoxetine, amitriptyline, nortriptyline, and imipramine;

H-2 antagonists such as nizatidine, cimetidine, famotidine, and ranitidine. Other classes of therapeutic agents for administration in accordance with this invention are anticonvulsants, antinauseants, muscle relaxants, anti-inflammatory substances, psychotropics, antimanics, stimulants, decongestants, antianginal agents, vasodilators, antiarrythmics, vascoconstrictors and migraine treatments, antiemetics, diuretics, antispasmodics, antiasthmatics, anti-Parkinson agents, expectorants, cough suppressants, mucolytics, vitamins, and mineral and nutritional additives.

One specific example in accordance with the present invention is the administration of a pelletized formulation of cefuroxime axetil coated to mask the notorious bitter taste of that compound upon oral administration. Cefuroxime axetil is formulated by an extrusion/marumerization process to form uniform pellets having an average size of about 400 to 1200 microns. The pelletized formulation is coated with the taste-masking agent Eudragit E. A 250 mg unit dose of the resulting pelletized formulation of cefuroxime axetil was supported in a delivery device with an angled screen substantially as shown in FIGS. 1-3. The ends of the tube were sealed to confine the pelletized dose between the angled grid and the sealed outlet end of the tube.

Prior to administration of the contained dose the outlet and inlet ends of the tube are opened by cutting away the heat sealed termini of the tube. The inlet end of the tube is placed in a glass of water and the outlet end of the tube is placed in the mouth of a patient who is asked to draw water into his mouth through the tube using a suction as associated with a normal sipping action. The dose of cefuroxime axetil is rapidly swept by the flow of water into the throat of the patient with minimal sensed contact with the oral cavity.

While providing particular advantage for oral administration of therapeutic agents to both pediatric and geriatric patients, it is expected that the methods and devices contemplated in accordance with this invention will find wide acceptance by a broad spectrum of patients who have experienced difficulty in swallowing traditional oral dosages in the forms of tablets and capsules.

I claim:

1. A unit dosage form of a therapeutic agent for oral administration comprising a therapeutic agent in a free-flowing form in an amount corresponding to a unit dose of said therapeutic agent, a tube for containing and administering said therapeutic agent to a patient, said tube having a liquid inlet end and a liquid outlet end, a grid located in said tube for supporting the dose between the two ends, said support grid having a surface area greater than the minimum luminal cross-sectional area of the tube along its length; and removable means for retaining the dose of therapeutic agent in the tube when the tube is not positioned for oral administration of the dose.

2. The unit dosage form of claim 1 wherein the support grid is constructed so that at least a portion of the grid forms an acute angle with a line parallel to the longitudinal axis of the tube.

3. The unit dosage form of claim 2 wherein the therapeutic agent is in the form of free-flowing particles having an average particle diameter of between about 100 and about 2000 microns.

4. In a device for the oral administration of a dose of a therapeutic agent in a flow of liquid drawn by a patient through a tube having an inlet end, an outlet end and a grid in the tube for supporting said dose between the tube ends, the improvement which comprises a grid formed to retain a therapeutic agent in particulate form and to have a surface area greater than the cross-sectional area of the tube at its outlet end.

5. The improvement of claim 4 wherein at least a portion of the grid forms an acute angle with a line parallel to the longitudinal axis of the tube.

6. The improvement of claim 4, wherein the grid presents a non-planar surface.

7. The improvement of claim 4 wherein the grid presents a planar surface.

8. The improvement of claim 7 wherein the grid is positioned to contact the tube at points on its internal diameter at varying distances from the outlet end.

9. The improvement of claim 4 wherein the grid is positioned in the tube closer to its outlet end than its inlet end.

10. The improvement of claim 4 wherein the inlet end is adapted to receive in fluid-sealing communication one end of a drinking straw.

11. The improvement of claim 4 wherein the outlet end is adapted to receive in fluid sealing communication one end of a drinking straw.

12. A method for oral administration of a therapeutic agent to a patient, said method comprising preparing said agent in pelletized or particulate form having a particle size between about 100 and 2,000 microns;

positioning said particles in an amount corresponding to a unit dose of said therapeutic agent on a grid positioned in a tube having an inlet end and an outlet end, and instructing the patient to position the outlet end of the tube in the patient's mouth and to draw liquid through said tube, whereby the therapeutic agent is carried by said fluid into the patient's alimentary canal with minimal sensed contact with the oral cavity.

13. A unit dosage form of an orally active therapeutic agent said dosage form comprising a tube having an inlet end and an outlet end and a grid positioned in said tube between said inlet and outlet ends, said grid having a surface area greater than the cross-sectional area of the tube at its outlet end and adapted to support particles having an average particle size between about 100 and 2000 microns, a therapeutic agent in the form of pellets or particles having an average size between about 100 and about 2,000 microns in an amount corresponding to a unit dose of said therapeutic agent, said agent located in the tube between the grid and the outlet end of the tube, and means for retaining said medication in said tube between the grid and the outlet end, wherein the inner diameter of the inlet and outlet ends of said tube are sized and the grid is constructed so that the rate of flow of fluid through the tube under the influence of a patient's normal sipping of fluids through said tube is sufficient to carry the therapeutic agent supported on said grid into the patient's alimentary canal with minimal sensed contact with the oral cavity.

14. A unit dosage form of a therapeutic agent for oral administration comprising:

a therapeutic agent in an amount corresponding to a unit dose of said therapeutic agent;

a tube for containing and administering said therapeutic agent to a patient, said tube having a liquid inlet end and a liquid outlet end, said tube having a longitudinal conformation loop such that when said tube is positioned for oral administration of the therapeutic agent there exists at least one axially discrete portion of said tube between the inlet end and the outlet end having a local gravitational potential minimum relative to adjacent axial portions of said tube, said axially discrete tube portion being sized to retain the dose of therapeutic agent when the tube is positioned for oral administration of the therapeutic agent; and removable means for retaining the therapeutic agent in the tube.

15. The unit dosage form of claim 14 wherein the therapeutic agent is in the form of free-flowing pellets or particles.

16. The unit dosage form of claim 15 wherein the particulate solid has an average particle diameter of between about 100 and about 2000 microns.

17. The unit dosage form of claim 14 wherein the therapeutic agent is in the form of a free-flowing particle suspension.

18. The unit dosage form of claim 14 wherein the therapeutic agent is in liquid form.

19. The unit dosage form of claim 14 wherein the liquid inlet end is adapted to receive in fluid-sealing communication one end of a drinking straw.

20. The unit dosage form of claim 14 wherein the liquid outlet end is adapted to receive in fluid-sealing communication one end of a drinking straw.

21. The unit dosage of claim 14 wherein the means for sealing the therapeutic agent in the tube comprises a tube pinching clip.

* * * * *